(12) United States Patent
Schmidt

(10) Patent No.: US 7,812,944 B1
(45) Date of Patent: Oct. 12, 2010

(54) ARRAY FOR OPTICAL EVALUATION OF AN OBJECT ARRAY

(75) Inventor: Stefan Schmidt, Jena (DE)

(73) Assignee: Carl Zeiss Jena GmbH (DE)

( * ) Notice: Subject to any disclaimer, the term of this patent is extended or adjusted under 35 U.S.C. 154(b) by 0 days.

(21) Appl. No.: 10/009,890

(22) PCT Filed: Apr. 13, 2000

(86) PCT No.: PCT/EP00/03306

§ 371 (c)(1),
(2), (4) Date: Apr. 8, 2002

(87) PCT Pub. No.: WO00/65325

PCT Pub. Date: Nov. 2, 2000

(30) Foreign Application Priority Data

Apr. 27, 1999 (DE) ................ 199 19 092

(51) Int. Cl.
*G01J 3/30* (2006.01)
(52) U.S. Cl. ...................... 356/317; 356/318
(58) Field of Classification Search ............. 356/317, 356/246, 318
See application file for complete search history.

(56) References Cited

U.S. PATENT DOCUMENTS

| | | | |
|---|---|---|---|
| 4,892,409 A | 1/1990 | Smith | |
| 5,112,134 A | 5/1992 | Chow et al. | |
| 5,355,215 A | 10/1994 | Schroeder et al. | |
| 5,867,266 A * | 2/1999 | Craighead | 356/344 |
| 5,876,672 A | 3/1999 | Dandliker et al. | |
| 5,962,852 A * | 10/1999 | Knuettel et al. | 250/339.11 |
| 6,133,986 A * | 10/2000 | Johnson | 355/67 |
| 6,144,455 A | 11/2000 | Tuunanen et al. | |
| 6,191,852 B1 | 2/2001 | Paffhausen et al. | |
| 6,411,835 B1 * | 6/2002 | Modell et al. | 600/407 |
| 6,424,404 B1 * | 7/2002 | Johnson | 355/44 |
| 6,534,011 B1 | 3/2003 | Karthe et al. | |
| 6,686,582 B1 | 2/2004 | Volcker et al | |
| 6,826,422 B1 * | 11/2004 | Modell et al. | 600/407 |

FOREIGN PATENT DOCUMENTS

| | | |
|---|---|---|
| DE | 19624421 | 6/1996 |
| DE | 19725050 | 6/1997 |
| DE | 19745373 | 10/1997 |
| DE | 19748211 A1 | 10/1997 |
| EP | 0841557 | 5/1998 |
| WO | WO96/23213 | 1/1996 |
| WO | 97/11354 | 3/1997 |
| WO | WO98/30889 | 7/1998 |
| WO | 98/48262 | 10/1998 |
| WO | 98/57151 | 12/1998 |

OTHER PUBLICATIONS

"Parallel, Confocal and Complete Spectrum Imager for Fluorescent Detection of High-Density Microarray", Valery Bogdanov et al, SPIE vol. 3605, Jan. 1999.

* cited by examiner

*Primary Examiner*—L. G Lauchman
(74) *Attorney, Agent, or Firm*—Eugene E. Renz, Jr.

(57) ABSTRACT

The invention relates to an array for optical evaluation of an object array, to which a microlens array (MLA), preferably an exchangeable and/or rotational microlens array, and a field lens with an illuminating device coupled by means of a beam splitter, preferably a rotational beam splitter, are pre-assigned in the direction of a detector array, wherein said illuminating device is coupled between the field lens and an objective.

14 Claims, 4 Drawing Sheets

Fluorescence reader

ARRAY FOR OPTICAL EVALUATION OF AN OBJECT ARRAY

CROSS REFERENCE TO RELATED APPLICATION

This application claims priority of German patent application no. 199 19092.5, filed Apr. 27, 1999, the complete disclosure of which is hereby incorporated by reference.

FIELD OF INVENTION

The invention relates to an arrangement for optical evaluation for an of an object array.

SUMMARY OF THE INVENTION

The invention provides for an arrangement for optical evaluation of an object array, comprising a detector array, a microlens array, which is disposed in front of the object array, as viewed in the direction of the detector array, a field lens, which is disposed in front of the object array, as viewed in the direction of the detector array, a light source, the radiation of which is coupled in by means of a beam splitter between the field lens and an objective, wherein the objective, together with the field lens, simultaneously images all pupils of the microlens array onto the detector array.

The invention will be explained in more detail below, by way of example and with reference to the drawings.

BRIEF DESCRIPTION OF THE DRAWINGS

The objects of the present invention and various features and details of the operation and construction thereof are hereinafter more fully set forth with reference to the accompanying drawings, in which.

DESCRIPTION OF THE BEAM PATH

Figure 1:
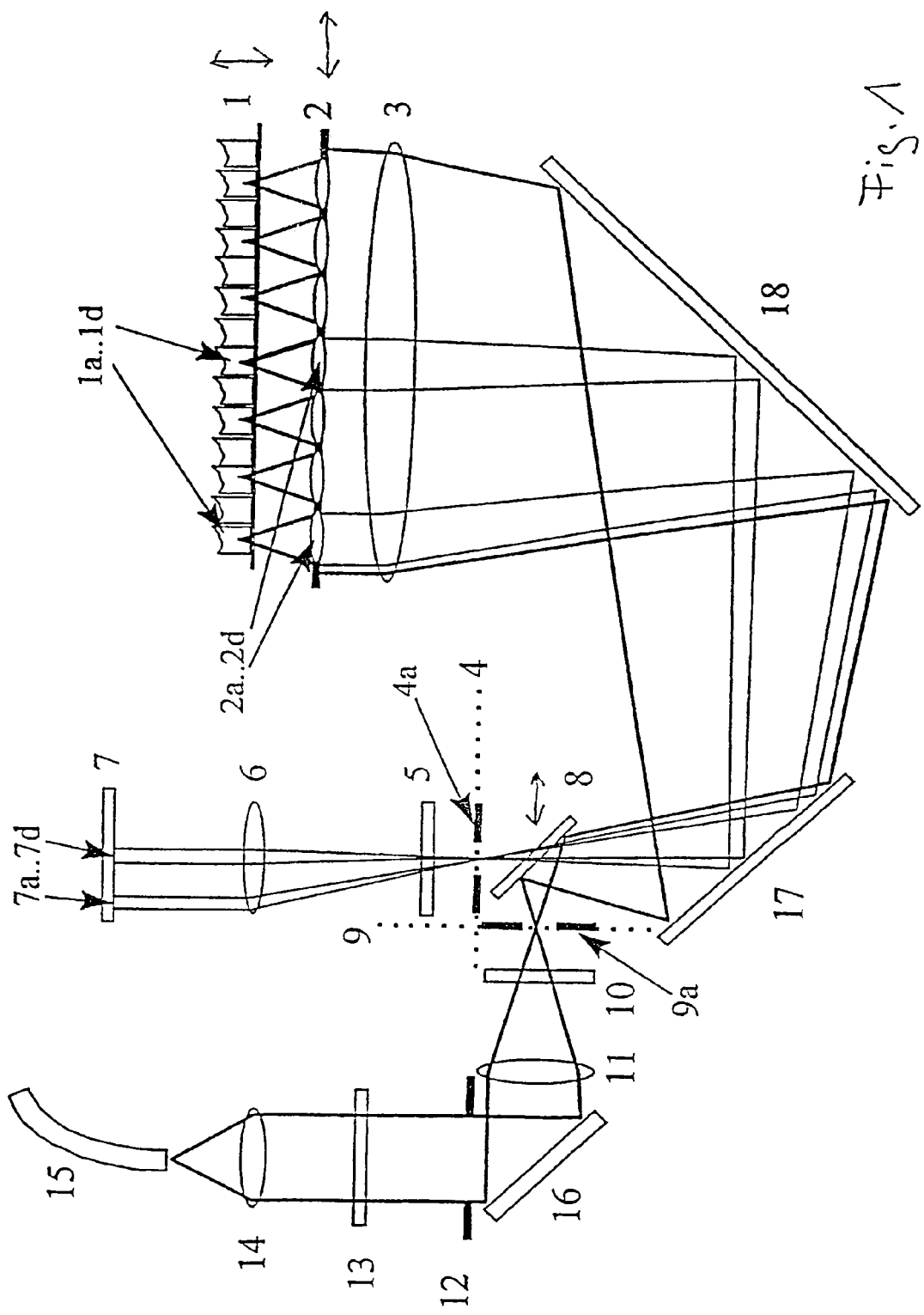
FIG. 1 shows the entire beam path, for example in fluorescence measurement.
Figure 2:
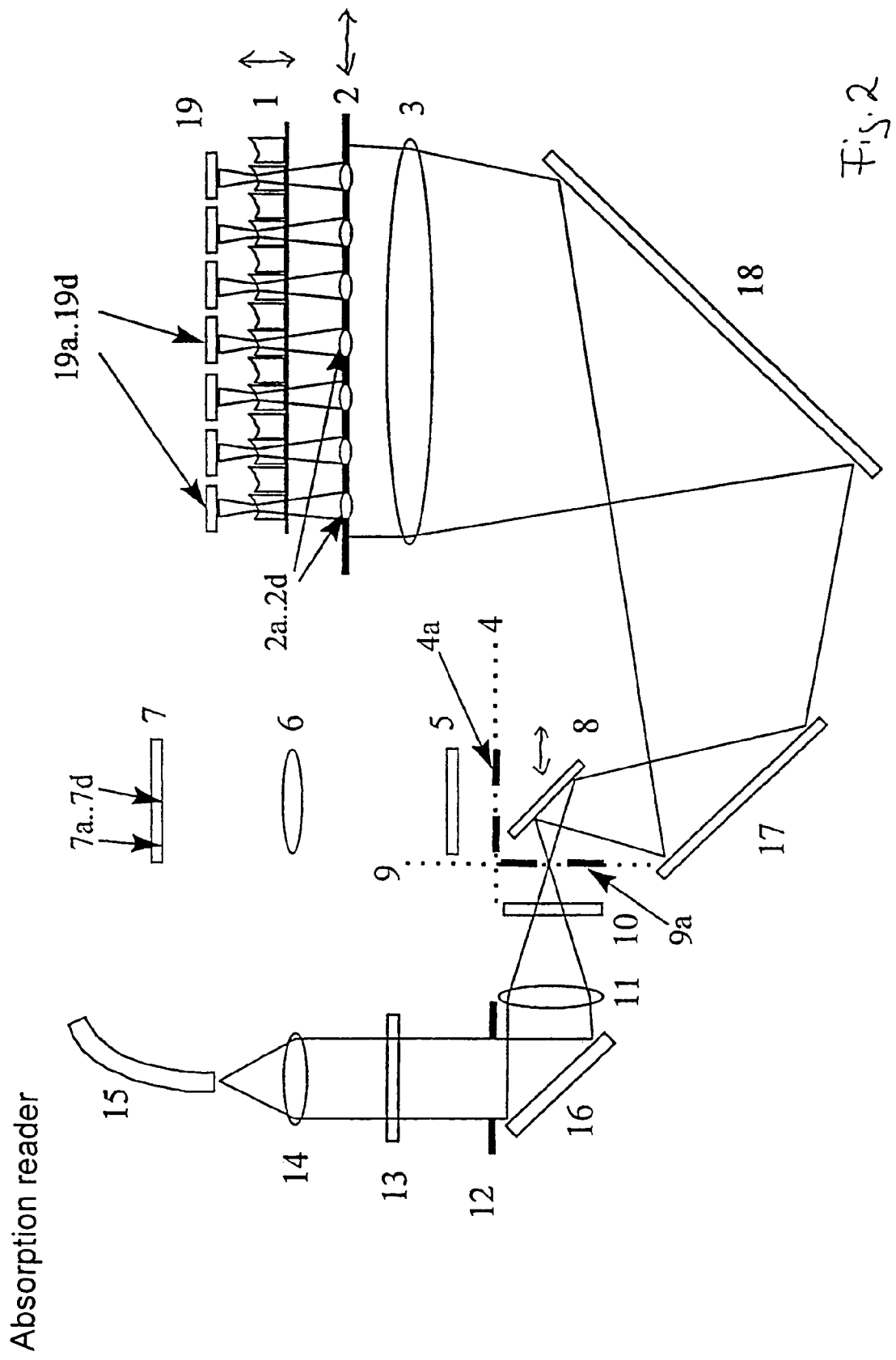
FIG. 2 shows the beam path in absorption measurement.
Figure 3:
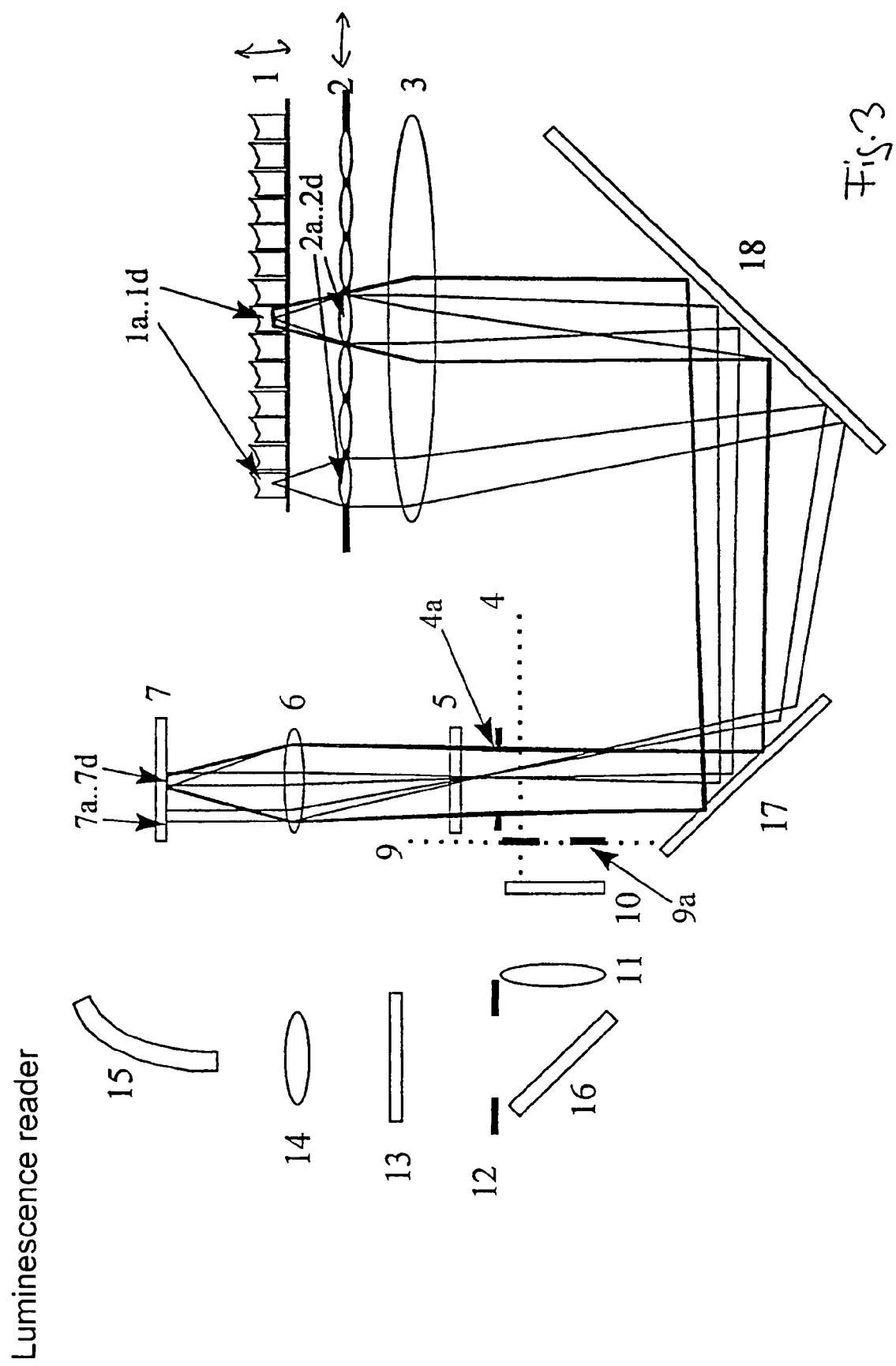
FIG. 3 shows the beam path in luminescence measurement.
Figure 4:
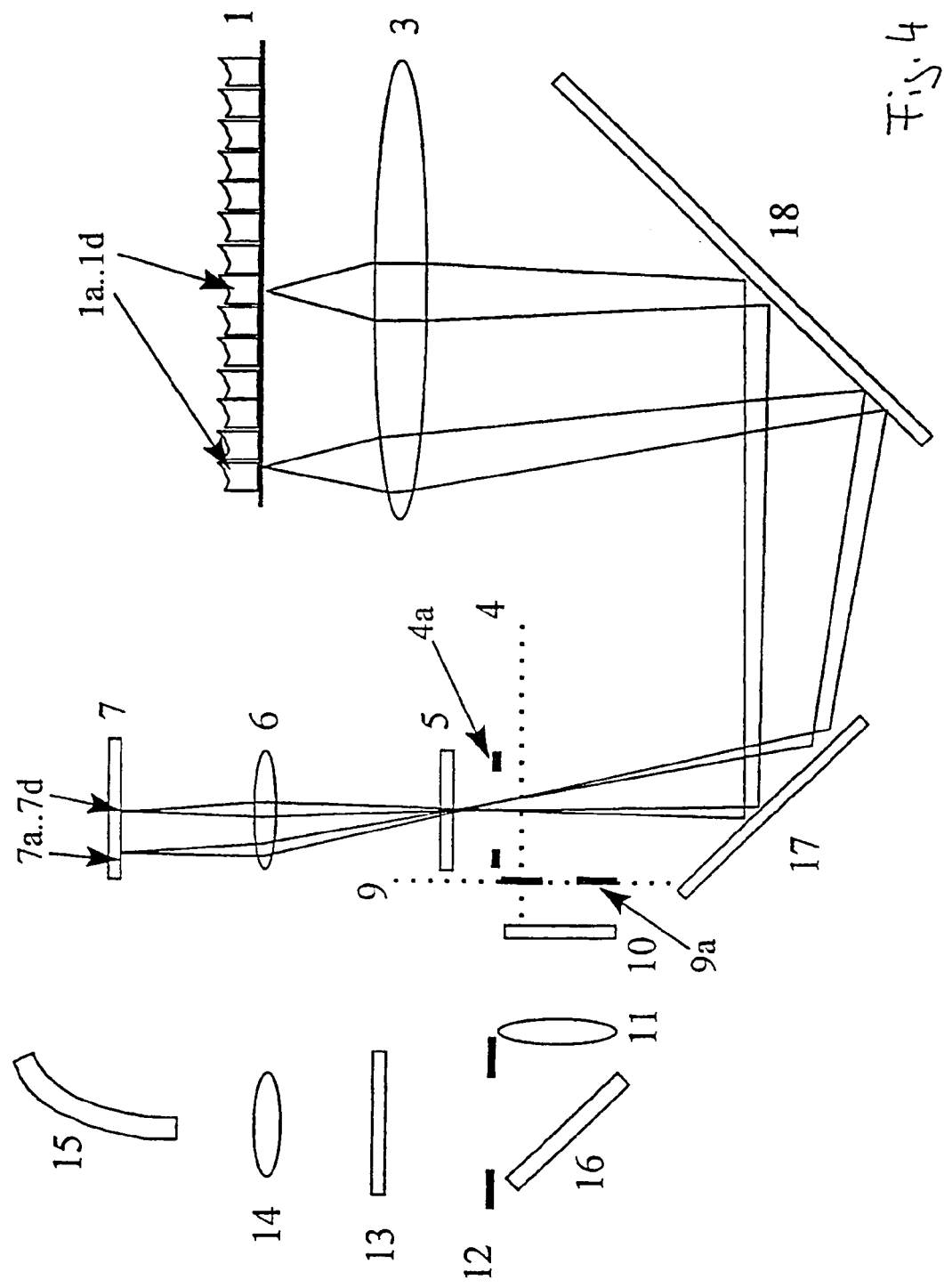
FIG. 4 shows the beam path without the MLA.

The optical assembly is divided into three essential components.

1. A microlens array (MLA) (2) for focusing light into small areas (sample volumes) of the wells (1a-1d) of a microtiter plate (MTP) (1), which are filled with a sample substance. In the case of fluorescence or luminescence applications, the MLA (2) also serves to collect light emitted from the sample volume.

2. A telescope arrangement of lenses 3, 11 and of a collimator (14) for illuminating the microlens array 2. As the light source, the output of an optical fiber may be used, or, as represented in the Figures, the lamp itself.

3. A field lens (3) and an objective (6) for telecentric imaging of the pupils of the MLA (2) on a CCD-array detector (7).

The microlens array consists of a regular arrangement of small lenses or objectives. Preferably, the the microlenses are arranged to form a rectangular grid. In any case, the arrangement of the microlenses is adapted to the geometry of the sample container array or of the MTP, respectively.

The front lens (3) of the telescope for illumination, which lens faces the MLA (2), also serves as field lens for the telecentric imaging of the MLA pupils.

1. The Excitation Beam Path

The light exiting from the optical fiber (15) is collected by a collimator (14). This collimator (14), together with the small telescope lens (11), which has a short focal length, images the optical fiber output into the intermediate image plane (9) of the telescope 3, 11. The large telescope lens (3), which has a long focal length, picks up the light from the intermediate image plane (9) and transforms it into a bundle of small divergence, by which the MLA (2) is illuminated on its side facing away from the sample. Each individual lens (2a ... 2d) of the MLA (2) then focuses the light into a respective well (1a ... 1d) of the microtiter plate (1).

The aperture diaphragm (12) of the illuminating telescope and attenuating filter (13) are disposed between the collimator (14) and the small telescope lens (11). The aperture diaphragm (12) defines the shape of the beam cross-section and keeps superfluous light away from the beam path. This serves to reduce signal cross-talk and scattered light background in the detection beam path. The aperture diaphragm (12) is disposed in a plane which is conjugated to the plane of the microlens pupils. Thus, the aperture lens (12) forms a small-scale copy of the external outline of the MLA (2). The aperture diaphragm (12) may also be embodied as a disk diaphragm array for improved reduction of scattered light.

The field diaphragm (9a) of the illuminating telescope is disposed in the intermediate image plane (9). The intermediate image plane (9) is imaged into the wells (1a ... 1d) of the MTP (1) by the large telescope lens (3) and the lenses (2a ... 2d) of the MLA (2). Thus, the field diaphragm (9a) defines the bundle cross-section of the light within the wells (1a ... 1d).

The excitation filter (10) serves to define the spectral range of the illumination.

The light from the samples is reflected into the beam path, which is also used for detection, via the mirror (8).

Arranging said mirror 8 in front of the objective 6 facilitates the selection of a different mode of illumination.

If the device is used for fluorescence analysis, the mirror (8) is designed as a dichroic beam splitter. The spectral range of the exciting light is reflected, while the spectral range to be detected is transmitted. If the device serves to detect luminescence, reflexion by the mirror 8 can be omitted as well as the illumination, and the beam path will then only comprise the detection beam path, as set forth below.

2. Detection Beam Path

The light emitted from the sample volume is collimated by the microlenses (2a ... 2d). One microlens (2a ... 2d) is assigned to each well (1a ... 1d) of the MTP (1). The collimated light exiting from the pupils of the microlenses is focused on the intermediate image plane (4), which is conjugated to the intermediate image plane (9) on the excitation side, by the large telescope lens (3), which also serves as field lens for pupil imaging. Thus, the images of the sample volumes from all wells (1a ... 1d) of the MTP (1) are superimposed in the intermediate image plane (4). The diaphragm (4a) defines the observed sample volume in each well. Preferably, the diaphragm (4a) is the same size as the field diaphragm (9a) of the illumination.

The diaphragm (4a) also constitutes the aperture diaphragm for pupil imaging. The imaging of the pupils of the microlenses (2a ... 2d) onto the CCD-array detector (7) is carried out by the objective (6).

The emission filter (5) serves to define the detected spectral range.

The reflecting mirrors (16, 17, 18) serve to bring the beam path into a compact shape. To this end, multiple folding by a multiplicity of mirrors is conceivable.

Description of Modes of Measurement

In principle, different methods of measurement are applicable to the samples contained in the MTP. Based on the above-described beam path, the measurements according to a method may be carried out in several wells at the same time. So far, the following methods of measurement have been taken into consideration:
1. Absorption
2. Fluorescence
3. Luminescence
4. Time-dependent fluorescence detection
5. Polarization-dependent fluorescence or absorption

Absorption

In absorption measurement, only the excitation beam path is used.

The beam splitter 8 may be replaced by a full mirror. The detection of the light transmitted through the sample is effected by means of a photodiode array (19), which is located as closely behind the sample containers as possible.

The above-described beam path allows the side of the MLA facing away from the samples to be homogeneously illuminated so that each well is traversed by light of the same intensity. For absorption purposes, the MLA is to be adapted such that the walls of the wells do not limit the beams formed by the microlens and that each light bundle impinges fully on its associated detector surface (19a . . . 19d) of the photodiode array.

This means that, for certain MTPs or sample containers, exchangeable MLAs and field diaphragms 9a may be provided, which are optimized with regard to their focal lengths and radiuses of curvature.

Fluorescence

In fluorescence measurement, excitation is effected in the same manner as in the case of absorption measurement. However, the mirror (8) is replaced by a dichroic beam splitter having high transmission for the light emitted by the sample.

The design of the MLA depends on the excitation, which should be as selective as possible, and on the detection of a small volume within the well, i.e. a sufficient chromatic correction requires a high numeric aperture (equal to, or greater than, 0.5).

Luminescence

Since the sample emits light by itself, only the detection beam path is used.

The beam splitter 8 may be swivelled out.

It is possible, in general and also in absorption measurements, to omit the MLA and to image an image of the MTP bottom directly onto the CCD-array detector. In this case, the entire plate can be read at once, regardless of the number of wells it contains. Although this means slight losses in sensitivity, all channels may be read simultaneously even where there are a large number of channels.

Fluorescence Detection Over Time

In time-dependent fluorescence detection, the same beam path is used as in fluorescence detection.

Excitation is effected by a light source capable of generating short light pulses (ca. 1 ns), i.e., for example, a suitable flash lamp.

The detector used should be capable of carrying out, after a delay of about the length of the excitation impulse, a measurement having an integration time of about the same length, synchronized to the illumination clock.

A microchannel-amplified camera is suitable for this purpose.

The intensity of fluorescence remaining after said delay is measured.

Polarization-Dependent Fluorescence

This requires a polarization-maintaining optical system. The fluorescence intensity in the polarization direction orthogonal to the excitation light is measured.

To this end, polarizing filters, which preferably polarize perpendicular to each other, may be provided in front of filters 5 and 10.

Although a certain preferred embodiment has been shown and described, it should be understood that many changes and modifications may be made therein without departing from the spirit and scope of the appended claims.

The invention claimed is:

1. Arrangement for optical evaluation of an object array (1) comprising
a detector array (7),
a microlens array (2), which is disposed in front of the object array (1), as viewed in the direction of the detector array (7),
a field lends (3), which is disposed in front of the object array (1) as viewed in the direction of the detector array (7),
a light source (15), the radiation of which is coupled in by means of a beam splitter (8) between the field lens (3) and an objective (6), wherein the objective (6), together with the field lens (3), simultaneously images all pupils of the microlens array (2) onto the detector array (7).

2. An arrangement as claimed in claim 1, wherein the field lens (3) and a further lens (11) form a telescopic arrangement which illuminates the object array (1) with light from the light source (15).

3. An arrangement as claimed in claim 1, comprising a diaphragm (4a) disposed between the field lens (3) and the objective (6), wherein the beam splitter (8) is located between the diaphragm (4a) and the field lens (3).

4. An arrangement as claimed in claim 1, wherein the field lens (3) and the objective (6) effect telecentric imaging of the pupil plane of the microlens array (2) onto the detector array (7).

5. An arrangement as claimed in claim 3, wherein one or more reflecting elements (17, 18) for folding the beam path for illumination and/or detection are provided between the field lens (3) and the diaphragm.

6. An arrangement as claimed in claim 1, wherein the object array (1) is slideable, at least vertically to the axis of illumination.

7. An arrangement as claimed in claim 1, wherein the light source (15) is intermittently switchable and a detection synchronized to the illumination clock, preferably a deferred detection, is possible so as to allow a time-dependent fluorescence measurement.

8. An arrangement as claimed in claim 7, comprising a flash lamp as the light source (15).

9. An arrangement as claimed in claim 1, wherein the microlens array (2) can be swiveled out of the beam path for observing the entire object array (1) and/or is exchangeable for adjustment to different measuring applications.

10. An arrangement as claimed in claim 1, wherein the light source (15) can be switched off for luminescence detection and/or a coupling element (8) for coupling in the radiation of the light source (15) can be swiveled out.

11. An arrangement as claimed in claim 1, wherein a second detector array is disposed behind the object array (1) in the illumination direction for absorption measurement.

12. Use of an arrangement as claimed in claim 1 in a combined device for measuring at least one of the following phenomena on the object array (1); fluorescence, time-dependent fluorescence, luminescence, and absorption.

13. The use of an arrangement as claimed in claim 1 as a reader for microtiter plates.

14. A method for the optical evaluation of an object array, the method comprising the steps of:
   providing an object array for optical evaluation;
   providing a detector array and a microlens array wherein said microlens array is disposed in front of said object array;
   providing a field lens disposed in front of the object array;
   generating an excitation light with an excitation light source which is coupled in by means of a beam splitter between a field lens and an objective lens; and
   simultaneously imaging all pupils of the microlens array onto the detector array by means of said objective lens together with said field lens.

* * * * *

UNITED STATES PATENT AND TRADEMARK OFFICE
CERTIFICATE OF CORRECTION

PATENT NO. : 7,812,944 B1
APPLICATION NO. : 10/009890
DATED : October 12, 2010
INVENTOR(S) : Stefan Schmidt It is certified that error appears in the above-identified patent and that said Letters Patent is hereby corrected as shown below:

Title page, item (54) and in the specification, column 1, the title should read "Arrangement for optical evaluation of an object array" (instead of "Array for optical evaluation of an object array).

Title page, item (75) the name of the city of the inventor Stefan Schmidt is Kiel, not Jena.

In the Specifications

Column 1, line 14 it should state "evaluation of an object array" (instead of "evaluation for an of an object array").

Column 1, line 61 should state "Preferably, the microlenses..." (instead of "Preferably, the the microlenses...").

Column 3, line 32 should state "by the microlenses..." (instead of "by the microlens...").

Column 4, line 32 should state "a field lens (3)..." (instead of a "filed lends...").

Signed and Sealed this
Twenty-fifth Day of June, 2013

Teresa Stanek Rea
*Acting Director of the United States Patent and Trademark Office*